(12) United States Patent
Ito et al.

(10) Patent No.: US 7,519,459 B2
(45) Date of Patent: Apr. 14, 2009

(54) DRIVING ASSISTANCE SYSTEM

(75) Inventors: Takafumi Ito, Toyota (JP); Hiroshi Uesugi, Nagoya (JP); Osamu Katayama, Nagoya (JP); Takashi Omori, Sapporo (JP); Kentaro Mizutani, Sapporo (JP)

(73) Assignees: DENSO CORPORATION, Kariya (JP); The National University Corporation Hokkaido University, Sapporo-shi (JP)

( * ) Notice: Subject to any disclaimer, the term of this patent is extended or adjusted under 35 U.S.C. 154(b) by 822 days.

(21) Appl. No.: 11/073,566

(22) Filed: Mar. 8, 2005

(65) Prior Publication Data

US 2005/0209749 A1     Sep. 22, 2005

(30) Foreign Application Priority Data

Mar. 17, 2004    (JP) ............................... 2004-077083

(51) Int. Cl.
G06F 7/00    (2006.01)
(52) U.S. Cl. .................... 701/36; 701/1; 340/425.5; 340/438; 340/439; 340/903; 348/148
(58) Field of Classification Search ................. 701/1, 701/36; 340/435, 441, 902, 903, 425.5, 438, 340/439; 348/148
See application file for complete search history.

(56) References Cited

U.S. PATENT DOCUMENTS 6,974,414 B2 * 12/2005 Victor ........................ 600/300

FOREIGN PATENT DOCUMENTS

| JP | A-H07-061257 | 3/1995 |
| JP | A-H08-178712 | 7/1996 |
| JP | A-2000-030199 | 1/2000 |
| JP | A-2002-083400 | 3/2002 |
| JP | A-2003-99899 | 4/2003 |
| JP | A-2004-178367 | 6/2004 |

OTHER PUBLICATIONS

Koike et al. "A Driver Model Based on Reinforcement Learning with Multiple-Step State Estimation." *IEICE*. vol. J84-D-II, No. 2. 2001. 370-379. (Discussed on pp. 10-11 in the specification).

S. Park et al. "Implementation of Visual Attention System Using Bottom-up Saliency Map Model, Artificial Neural Networks and Neural Information Processing." *ICANN/ICONIP, LNCS 2714*. 2003. 678-685. (Discussed on p. 14 in the specification).

Office Action dated Jul. 1, 2008 in corresponding Japanese patent application No. 2004-077083 (and English translation).

* cited by examiner

*Primary Examiner*—Gertrude Arthur Jeanglaud
(74) *Attorney, Agent, or Firm*—Posz Law Group, PLC

(57) ABSTRACT

A driver's gaze distribution is detected. Based on the detected distribution, an image corresponding to a driver's visual-field is extracted from images photographed by a front monitor camera and is accumulated. A first driver's gaze probability distribution necessary for steering operation is computed based on the accumulated images, and a second driver's gaze probability distribution that is expected is computed based on visual characteristics within the images. An ideal gaze probability distribution is obtained by adding up the first and the second probability distributions. Presence of a risk is determined when the difference between the driver's gaze and the ideal gaze probability distribution becomes a given threshold. A windshield display or a speaker outputs the determined result.

11 Claims, 5 Drawing Sheets

DRIVING ASSISTANCE SYSTEM

CROSS REFERENCE TO RELATED APPLICATIONS

This application is based on and incorporates herein by reference Japanese Patent Application No. 2004-77083 filed on Mar. 17, 2004.

FIELD OF THE INVENTION

The present invention relates to a driving assistance system that assists a driver to operate a vehicle.

BACKGROUND OF THE INVENTION

Recently, various driving assistance systems become available. For instance, Patent Document 1 describes a driving assistance system that computes a degree of driving behavior risk by using a gaze of a driver.

Patent Document 1: JP-2003-99899 A

In detail, in a first system in Patent Document 1, a computation unit for a degree of driving behavior risk determines a traveling direction of a subject vehicle based on steering angles detected by a steering angle sensor. Further, this unit computes the risk degree by checking how long or how frequent the driver sees the traveling direction from a given time point before to the present time using behavior of the driver's gaze grouped with a gaze filter. For instance, the driving behavior risk decreases when the driver sees the traveling direction more than a given threshold period or more than a given threshold frequency. In contrast, the risk increases when the driver does not see the traveling direction more than a given threshold period or more than a given threshold frequency.

Further, in a second system in Patent Document 1, a computation unit for a degree of driving behavior risk determines whether a driver's gaze is on an object that is obtained from photographing images outside the vehicle and should be recognized by the driver. The computation unit then computes the risk degree by considering various parameters. For instance, the driving behavior risk decreases when the driver's gaze is on a bicycle approaching the subject vehicle, while the risk increases when the gaze is not on the bicycle.

In the above first system, whether a driver sees the traveling direction is determined based on not only the driver's visual behavior at the present time but also that in the past. In contrast, in the second system, the degree of the driving behavior risk is determined without considering the visual behavior in the past. In general, a person's visual memory remains for a given period. Suppose a case that a driver does not see an object at a moment when the degree of the risk is determined. Even in this case, the risk degree often decreases if the driver saw the object just before the moment. In contrast, continuing observing the object based on the instruction of the system may cause a secondary risk.

SUMMARY OF THE INVENTION

It is an object of the present invention to provide a driving assistance system that is capable of solving the above-described problem to thereby properly perform driving assistance. Namely, in this system, whether a driver needs to see an object is determined based on not only the present visual behavior but also visual behavior in the past.

To achieve the above object, a driving assistance system mounted in a vehicle is provided with the following. A distribution of a driver's gaze is detected. An ideal probability distribution of a driver's gaze is computed from the distributions detected in a past and information, wherein the information is derived from the vehicle and a periphery surrounding the vehicle. Presence of a risk is determined when a difference between the detected distribution and the computed probability distribution exceeds a given threshold. Further, a determined result is outputted.

In this structure, the actual driver's gaze distribution and the ideal gaze probability distribution are compared with each other. For instance, in a case that a driver does not see an obstacle present on a road and the driver should recognize the obstacle, it can be notified that there is a risk because of the obstacle present ahead of the vehicle.

Further, when a driver does not see a sharp curve ahead of the traveling direction, it can be notified that there is a risk because of the sharp curve present ahead of the traveling direction.

Further, the driver's ideal gaze probability distribution can be computed not only by using the present image information, but also by using the image information in the past. For instance, in a case that the driver sees the obstacle or the sharp curve once, the notification of the risk is not outputted for the following given period even though the driver sees the position no more. Therefore, this helps prevent a secondary risk that may occur because the driver continues observing the specific object.

BRIEF DESCRIPTION OF THE DRAWINGS

The above and other objects, features, and advantages of the present invention will become more apparent from the following detailed description made with reference to the accompanying drawings. In the drawings:.

DETAILED DESCRIPTION OF THE PREFERRED EMBODIMENTS

Figure 1:
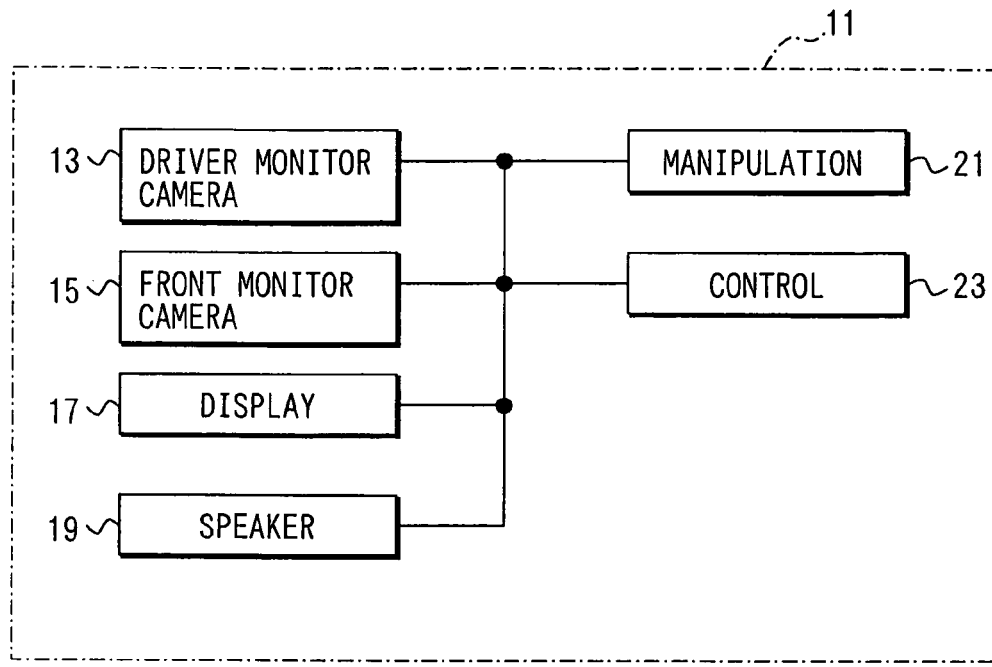
FIG. 1 is a block diagram of a schematic structure of a driving assistance system according to an embodiment of the present invention.

A driving assistance system 11 according to an embodiment of the present invention is shown in FIG. 1 regarding its schematic structure. The system is provided in a subject vehicle and consists of a driver monitor camera 13, a front monitor camera 15, a windshield display 17, a speaker 19, a manipulation unit 21, and a control unit 23.

The driver monitor camera 13 photographs the face of a driver to detect a driver's gaze, and is preferably provided with a capability of emitting infrared light and photographing the reflected lights for use in darkness.

The front monitor camera 15 is disposed in the front end of the vehicle (e.g., at the bumper) or in the front portion within the vehicle compartment (e.g., at the rear of a rearview mirror) as an imaging unit to photograph an area corresponding to a driver's visual-field in a traveling direction of the vehicle.

The windshield display 17 displays various information in the front windshield to notify the driver of information. The display 17 includes a type that projects light on the windshield and a type that is combined with an emitting member attached to or contained in the windshield for emitting light.

The speaker 19 outputs various guiding sounds or alarms. The manipulation unit 21 is used for the driver to input various instructions and is a mechanical switch or a touch panel integrated with a screen of a liquid crystal display (not shown).

The control unit 23 consists of a CPU, a ROM, a RAM, and a bus connecting the foregoing components. It receives signals from the driver monitor camera 13, the front monitor camera 15, and the manipulation unit 21 to thereby execute various processes, and controls the windshield display 17 and the speaker 19 based on the results from the executions.

Figure 2:
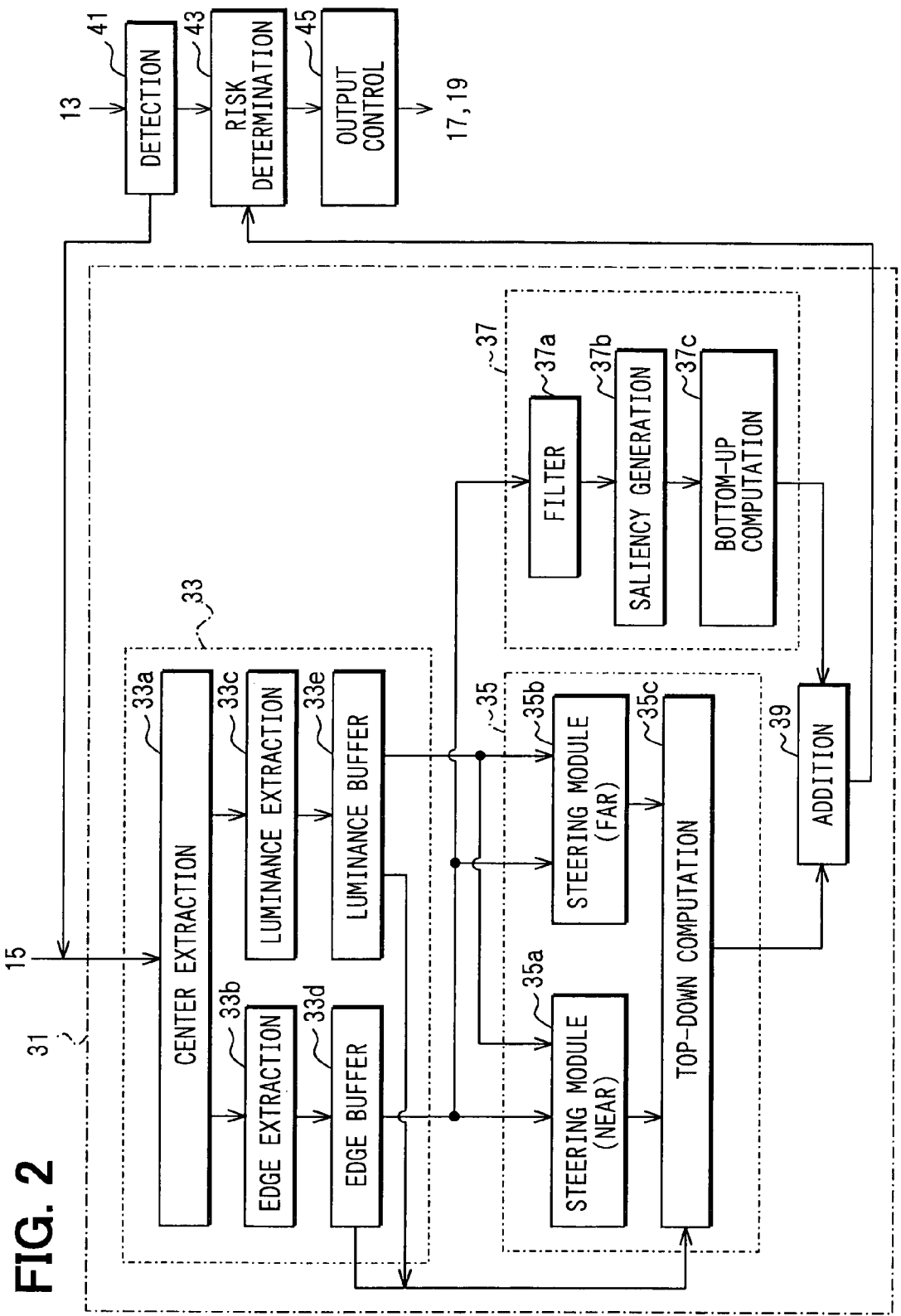
FIG. 2 is a block diagram showing functions of a control unit.

In detail, as shown in FIG. 2, the control unit 23 includes an ideal gaze probability distribution computation unit 31, a gaze distribution detection unit 41, a risk determination unit 43, and an output control unit 45.

The gaze distribution detection unit 41 detects a distribution of a driver's gaze by receiving image signals from the driver monitor camera 13, and outputs the detected result to the risk determination unit 43 and the ideal gaze probability distribution computation unit 31.

The ideal gaze probability distribution computation unit 31 computes an ideal gaze probability distribution by receiving image signals from the front monitor camera 15 and the gaze distribution detection unit 41, and outputs the computed result to the risk determination unit 43.

The risk determination unit 43 determines a risk by receiving signals from the gaze distribution detection unit 41 and the ideal gaze probability distribution computation unit 31, and outputs the determined result to the output control unit 45.

The output control unit 45 computes signals by receiving signals from the risk determination unit 43 to send the computed signals for controlling the display 17 and the speaker 19.

Next, detail explanation will be described below regarding the gaze distribution detection unit 41, the ideal gaze probability distribution computation unit 31, the risk determination unit 43, and the output control unit 45.

1. Gaze Distribution Detection Unit 41

The gaze distribution detection unit 41 obtains a gaze distribution that plots, for a given period, the entire positions of the driver's gazes that are obtained every given intervals. In detail, the gaze distribution detection unit 41 determines a position of a driver's eye by conducting pattern matching to the images inputted from the driver monitor camera 13. It then detects a center of the iris from the regional image of the determined position of the driver's eye by using an elliptic approximation, and further obtains a gaze vector based on the detected center. Another method for obtaining the gaze vector can be used that obtains the gaze vector from center coordinates of the pupil. The thus-obtained gaze vector is used to obtain a gaze distribution (e.g., for two seconds in the past). The obtained distribution is outputted to the ideal gaze probability distribution computation unit 31 and the risk determination unit 43.

2. Ideal Gaze Probability Distribution Computation Unit 31

The ideal gaze probability distribution computation unit 31 computes an ideal gaze probability distribution that is a probability distribution of ideal driver's gaze necessary for safely driving the subject vehicle. The ideal gaze probability distribution computation unit 31 mainly includes a visual-field-image accumulation unit 33, a first gaze probability distribution computation unit 35, a second gaze probability distribution computation unit 37, and an addition unit 39.

(1) Visual-Field-Image Accumulation Unit 33

In the visual-field-image accumulation unit 33, a visual-field center-image extraction unit 33a extracts an image (visual-field image) corresponding to a visual-field having a gaze as a center, by using information of a distribution of a driver's gaze that the gaze distribution detection unit 41 detects at the same timing, from among photographed images inputted from the front monitor camera 15. This visual-field image Img is expressed by Formula 1. Here, a gaze position (visual-field center) is Xeye (t), a distance from the gaze position is r, and a radius of the visual-field is R:

$$Img(r,\theta,Xeye(t)), r \leq R \qquad \text{Formula 1}$$

Next, an edge extraction unit 33b extracts an edge portion from the visual-field image Img extracted by the visual-field center-image extraction unit 33a, and conducts an inversely proportional process, where a resolution of the image becomes inverse proportional to the distance r, to generate an edge image Edge. In the inverse proportional process, the resolution of the image decreases as the corresponding position departs towards the peripheral regions from the visual-field center. The edge image Edge is expressed by Formula 2 as follows:

$$Edge(r,\theta,Xeye(t)), r \leq R \qquad \text{Formula 2}$$

Next, the edge extraction unit 33b accumulates the edge images Edge in an edge buffer 33d. Here, the edge buffer 33d can accumulate images having the same size of the image that the front monitor camera 15 inputs, and overwrite with the gaze position being associated with the relevant position within the image. Further, information of the edge buffer 33d attenuates while time elapses. The information having no input for a given period disappears. This relation is expressed using a time constant τ by Formula 3.

$$\tau_{Buf} d/dt \text{Buffer}(X,t) = -\text{Buffer}(X,t) + Edge(r, \theta, Xeye(t)) \qquad \text{Formula 3}$$

Figure 3:
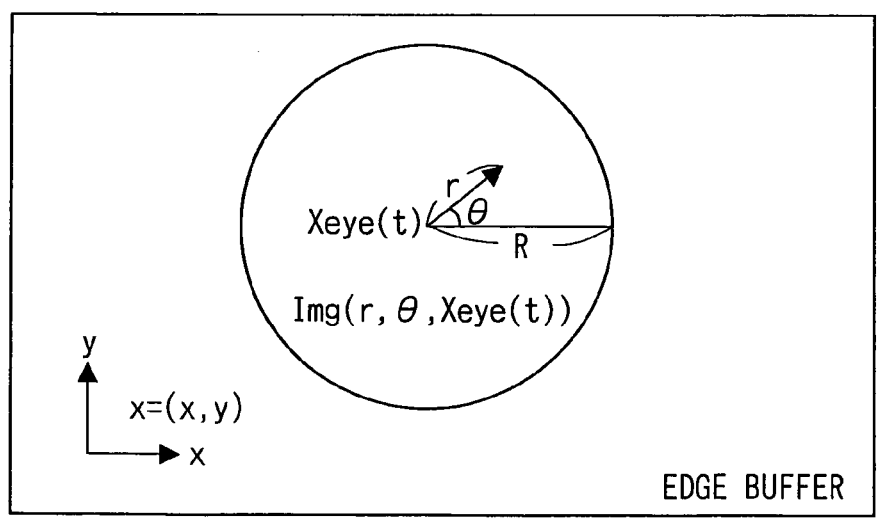
FIG. 3 is a diagram explaining a relationship between a visual-field image and an edge buffer.

Further, the edge buffer 33d includes a time index to retain timing when information of each position is inputted. Here, the relation between the visual-field image Img and the edge buffer 33d will be explained with reference to FIG. 3. As explained above, the edge buffer 33d accumulates images having the same size as that of the image photographed by the front monitor camera 15, so the visual-field image Img as a partial image within this size is sequentially overwritten and accumulated on the edge buffer 33d.

A luminance extraction unit 33c extracts a portion having high luminance (or high brightness) from among the visual-field image Img extracted by the visual-field center-image extraction unit 33a, and conducts an inverse proportional process where a resolution of the extracted image becomes inverse proportional to the distance r to generate an luminance image Int. The inverse process the resolution of the extracted image decreases as the corresponding position departs to the peripheral regions from the visual-field center. This luminance image Int is expressed by Formula 4.

$$Int(r,\theta,Xeye(t)), r \leq R \qquad \text{Formula 4}$$

The luminance extraction unit 33c causes a luminance buffer 33e to accumulate the luminance image Int. The luminance buffer 33e can accumulate the same size of the image as that of the image photographed by the front monitor camera 15 and overwrite with the gaze position being associated with the relevant position within the image. Further, information of the luminance buffer 33e attenuates while time elapses. The information having no input for a given period disappears. This relation is expressed using a time constant τ by Formula 5.

$$\tau_{Buf} d/dt \text{Buffer}(X,t) = -\text{Buffer}(X,t) + Int(r,\theta, X eye(t)) \quad \text{Formula 5}$$

Further, the luminance buffer 33e includes a time index to retain timing when information of each position is inputted.

(2) First Gaze Probability Distribution Computation Unit 35

The first gaze probability-distribution computation unit 35 computes a gaze probability distribution (top-down gaze probability distribution) by obtaining road shapes from the image information accumulated by the visual-field image accumulation unit 33. The gaze probability distribution (top-down gaze probability distribution) indicates a requirement degree of gaze movement for operating the steering. Namely, the gaze probability distribution indicates which position a gaze should be directed to for the steering operation. Here, the road shapes include a road width and a road curve. These are obtained from white line painted along the ends of a road width, a road center divider, or the like.

The inventors uses as a driver's steering operation model a driving model based on reinforcement learning proposed by Koike et al. "A Driver Model Based on Reinforcement Learning with Multiple-Step State Estimation" in Vol. J84-D-II, No. 2, pp. 370-379, 2001, IEICE (Institute of Electronics, Information and Communication Engineers). Koike et al. propose the relation between the road curve and the gaze movement.

The driver's steering operation model includes an estimation module that outputs a steering operation amount, and a reinforcement learning module that determines the eventual steering operation amount. The estimation module estimates positions at present, one second later, two seconds later, and three seconds later and obtains distances to the subject vehicle from the both ends of the road corresponding to the individual positions, to thereby compute and output the steering operation amounts necessary for stably operating the subject vehicle at the individual time points. The reinforcement learning module determines the eventual steering operation amount from among the steering operation amounts at the individual positions or time points based on the road conditions.

This embodiment uses a steering module (near) 35a that estimates a position at one second later and a steering module (far) 35b that estimates a position at three seconds later. Each steering module outputs information request (top-down gaze request) for a visual input necessary for inputting to each steering module itself. Gaze movement requests corresponding to the outputted positions are thereby computed as a probability distribution.

In the first gaze probability-distribution computation unit 35, the steering modules 35a, 35b output individual gaze positions. The top-down gaze probability-distribution computation unit 35c computes a top-down gaze position by using a time index generated by adding up the outputted gaze requests and the time indices of the edge buffer 33d and the luminance buffer 33e, as shown in Formula 6.

$$Eye_{TD}(X, t) = \quad \text{Formula 6}$$
$$\text{Buffertime}(X, t) \times \Sigma \alpha_i \times \exp(-((X - Xi(t))/\sigma_{TD})^2)$$

$Eye_{TD}(X, t)$: Top-down Gaze Request
$\text{Buffertime}(X, t)$: Time Index
$\alpha_i$: Selection Signal of each Module $i$
$Xi(t)$: Gaze Request Position
$\sigma_{TD}$: Top-down Gaze Region Thus, the larger gaze requests are obtained as the corresponding positions have the older updated times in the buffer by multiplying the time indices corresponding to the positions. Here, the position to which the gaze has not been directed for a long period potentially changes from the actual forward image. Thus, this formula outputs to the driver a strong request of the gaze movement towards the position to which the gaze has not been directed for a long period. Further, the top-down gaze probability-distribution computation unit 35c normalizes the computed gaze requests within the entire visual area to thereby compute and output a top-down gaze probability distribution as follows.

$$P_{EyeTD}(X, t) = Eye_{TD}(X, t) \Big/ \sum_{allx} Eye_{TD}(X, t) \quad \text{Formula 7}$$

$P_{EyeTD}(X, t)$: Top-down Gaze Probability Distribution

Figure 4A:
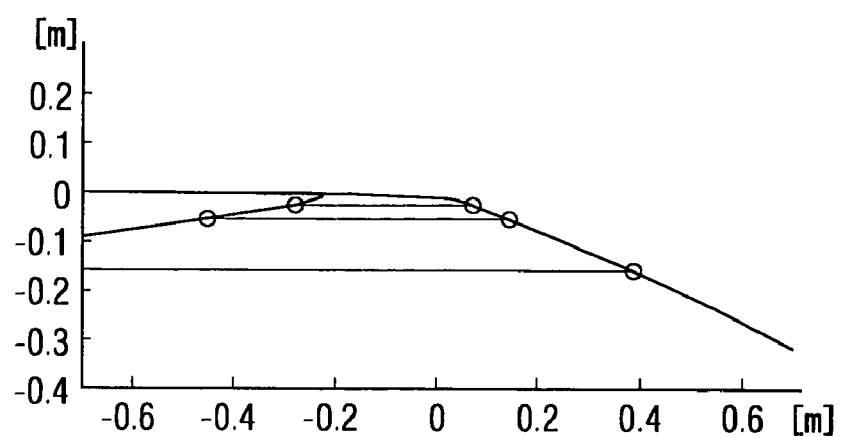
FIG. 4A is a photographed image of a road indicated by a wire frame.
Figure 4B:
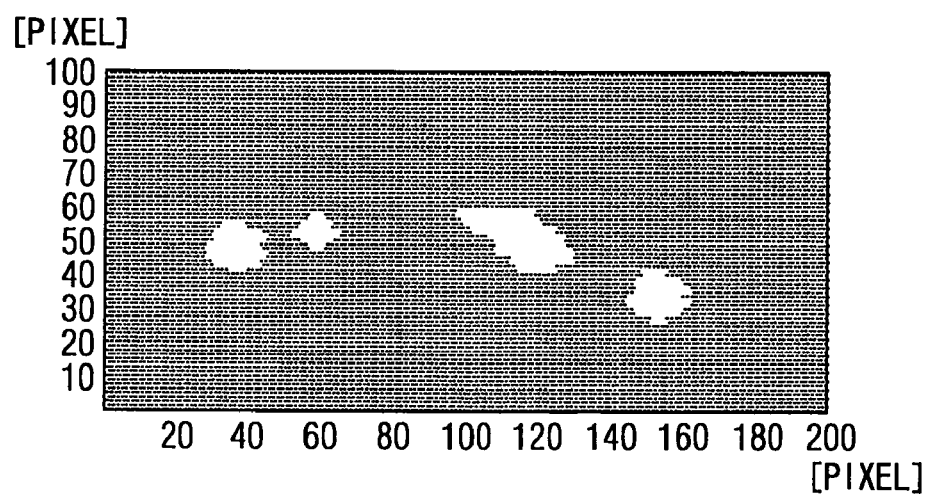
FIG. 4B is a view showing a top-down gaze probability distribution obtained from the image in FIG. 4A.

An example of the top-down gaze probability distribution is explained with reference to FIGS. 4A, 4B. FIG. 4A is an image photographing a road by a wire frame, while FIG. 4B shows a top-down gaze probability distribution obtained from the photographed image in FIG. 4A. In FIG. 4A, horizontal lines show expected positions one second later, two seconds later, and three seconds later (in this embodiment, position two seconds later is not used for computing). The circles in both ends of the horizontal lines show largeness or widths of the gaze requests. In FIG. 4B, brightness shows a probability distribution of the gaze requests, so the whiter portion is higher in the gaze requests.

(3) Second Gaze Probability Distribution Computation Unit 37

The second gaze probability-distribution computation unit 37 computes a gaze probability distribution (bottom-up gaze probability distribution) that indicates a strength in passive gaze movement of a driver based on characteristics (visual characteristics) of the visual inputs. Namely, the second gaze probability distribution computation unit 37 preferably computes a probability distribution of positions that a driver naturally sees from their visual characteristics (e.g., brightness). In general, initial visual receptive cells such as a retina and a lateral geniculate body has a sensitivity of high resolution to an input on a narrow central region of the receptive visual-field, but shows inhibited response to an input on a peripheral region of the receptive visual-field. This nature achieves differentiation processing in space and is suitable for detecting a salient portion or discontinuity in the image within the visual-field. This embodiment uses a model based on this initial visual structure, for generating a visual saliency map, and computes a gaze probability distribution indicating the strength in the receptive gaze movement based on the characteristics of the visual inputs.

The computation for this probability distribution is proposed by S. Park et al. "Implementation of Visual Attention System Using Bottom-up Saliency Map Model, Artificial Neural Networks and Neural Information Processing—ICANN/ICONIP 2003, LNCS 2714, pp. 678-685, Nov. 20, 2003. " Here, the visual characteristics include an edge strength, brightness (or luminance), and a color difference. Here, the visual characteristics further include color saturation and an optical flow.

In detail, the filter unit 37a gradates the image of the edge buffer 33d into four steps using a Gaussian filter. The saliency map generation unit 37b generates a saliency map by the following. The unit 37b treats the gradated images as pseudo peripheral images, adds up and normalizes images that compute difference from the images of the previous step.

Next, the bottom-up gaze probability-distribution computation unit 37c normalizes the saliency map in the entire visual region to thereby compute a bottom-up gaze probability distribution as follows.

$$P_{EyeBU}(X, t) = SM(X, t) / \sum_{allx} SM(X, t)$$ Formula 8

$SM(X, t)$: Saliency MAP

Here, to prevent a gaze from continuing fixing to or observing one position to which the gaze is directed once, it is preferable that the gaze is moved to another position by attenuating the visual probability distribution. Refer to Formula 9.

$$P_{EyeBU}(X,t)=0, X \in (r, \theta, Xeye(t)), r \leq R$$ Formula 9

Figure 5A:
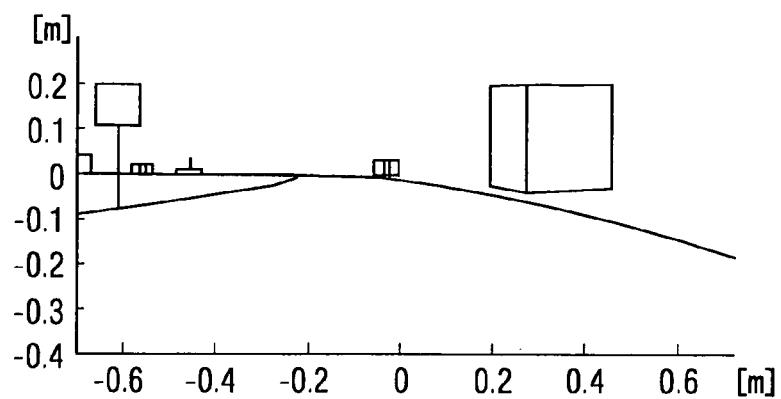
FIG. 5A is a photographed image of a road indicated by a wire frame.
Figure 5B:
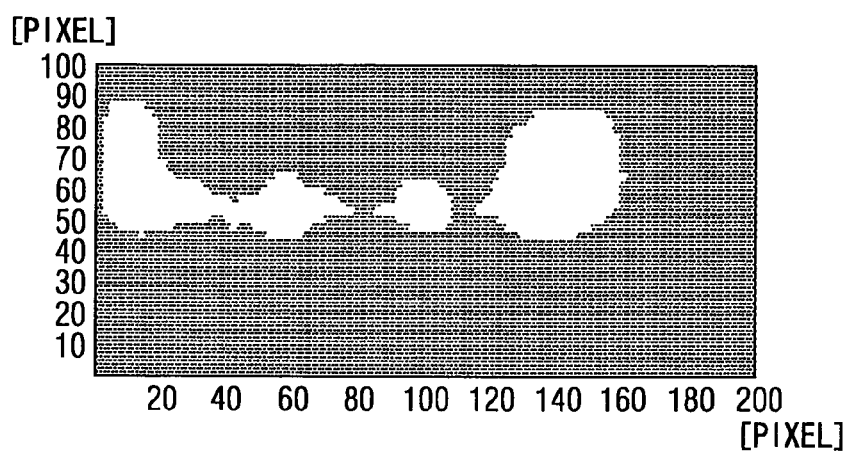
FIG. 5B is a view showing a bottom-up gaze probability distribution obtained from the image in FIG. 5A.

Here, an example of the bottom-up gaze probability distribution will be explained with reference to FIGS. 5A, 5B. FIG. 5A is an image photographing a road by a wire frame, while FIG. 5B shows a bottom-up gaze probability distribution obtained from the photographed image in FIG. 5A. In FIG. 5A, a road sign is shown on the left of a road, while a building is on the left. In FIG. 5B, brightness shows a visual probability, so the whiter portion is higher in the gaze probability.

(4) Addition Unit 39

The addition unit 39 computes an ideal gaze probability distribution by adding up the top-down gaze probability distribution computed by the first gaze probability-distribution computation unit 35 and the bottom-up gaze probability distribution computed by the second gaze probability-distribution computation unit 37 as follows.

$$P_{Eye}(X,t) = (P_{eyeTD}(X,t) + P_{eyeBU}(X,t)) \times \frac{1}{2}$$ Formula 10

3. Risk Determination Unit 43

Figure 6:
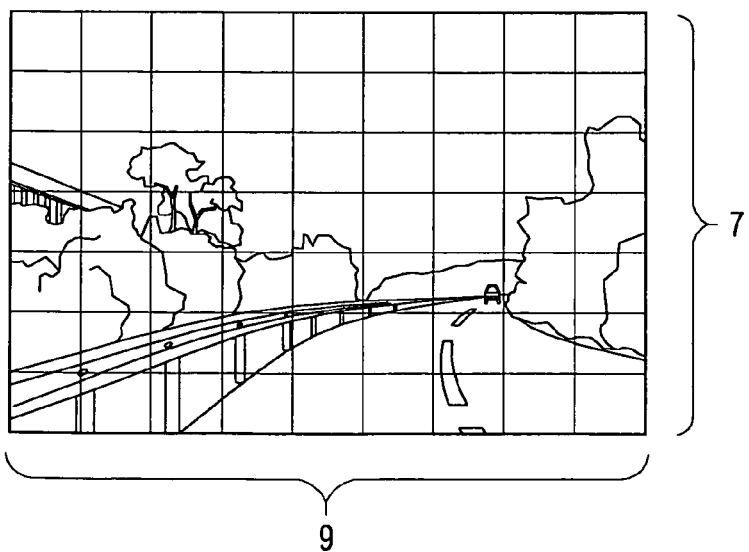
FIG. 6 is an image that is divided into portions of n rows x m columns.

The risk determination unit 43 divides the same size (region) as that of the image photographed by the front monitor camera 15 into meshes (sub-regions) of n rows×m columns. (Refer to the image in FIG. 6, where the region is divided into 7 rows×9 columns.) The risk determination unit 43 then obtains a gaze distribution Pmd (n, m) with respect to each sub-region based on the gaze distribution outputted from the gaze distribution detection unit 41. Further, the risk determination unit 43 obtains an ideal gaze probability distribution Pmi (n, m) with respect to each sub-region based on the ideal gaze probability distribution outputted from the ideal gaze probability distribution computation unit 31. Then, the risk determination unit 43 computes difference diff (n, m) between the foregoing two distributions Pmd, Pmi, with respect to each sub-region as follows.

$$diff(n,m) = Pmi(n,m) - Pmd(n, m)$$ Formula 11

Next, risk degrees dng (n, m) of each region is obtained using the obtained distribution difference diff (n, m) by the determination formula of Formula 12.

if $diff(n,m)$>const $dng(n,m)=diff(n,m)$ else $dng(n, m)=0$ Formula 12

This determination formula means that, while n and m are varied, the risk degree dng (n, m) is the difference diff (n, m) when the difference diff (n, m) is more than a given value (threshold), while the degree dng (n, m) is zero when the difference diff (n, m) is not more than the given value. This sub-region can be named as a not-cared region or position to which a driver does not pay attention for a while.

4. Output Control Unit 45

Figure 7A:
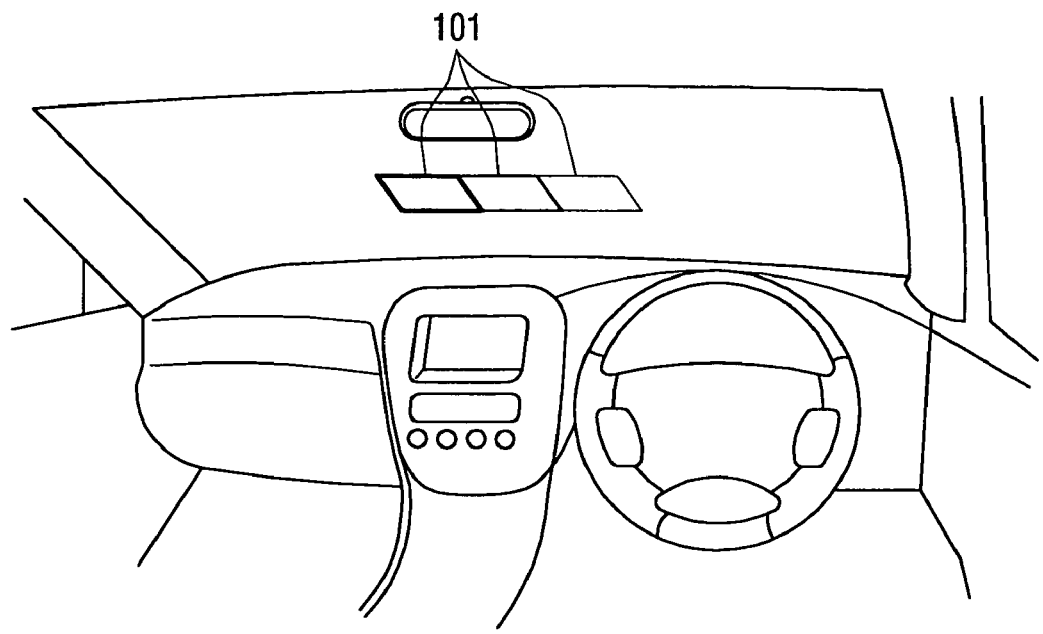
FIG. 7A is a view of the front portion of a vehicle compartment.
Figure 7B:
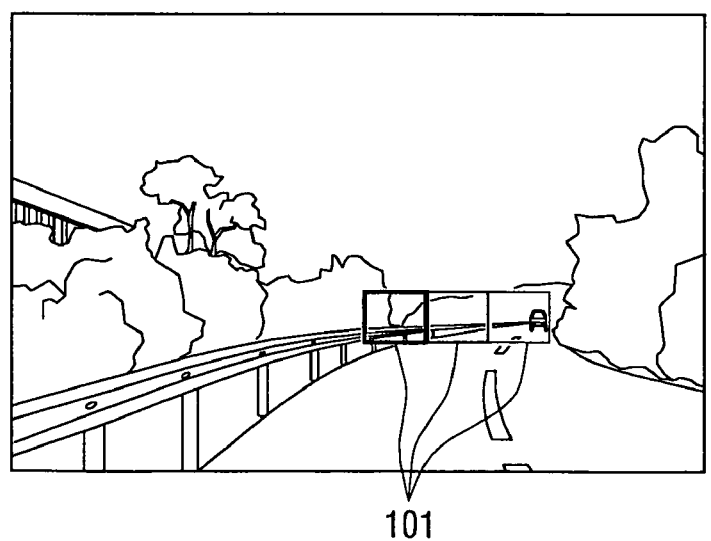
FIG. 7B is an image of a scenery that a driver sees.

The output control unit 45 sends signals for controlling the windshield display 17 and the speaker 19 based on the risk degree dng (n, m) inputted from the risk determination unit 43. In detail, as shown in FIG. 7A, the output control unit 45 displays rectangular markers 101 defining the regions or sub-regions having the high risk degrees dng (n, m) (as the not-cared sub-region) while superimposing them on the front windshield. Here, the marker 101 is displayed so that the driver (or the position of the driver's gaze) can see the relevant object or position that should be seen by the driver through the portion of the windshield marked by the marker 101. Further, the marker can be transparently colored or an arrow instead. The marker 101 can be changed in visual characteristics such as color depending on the risk degree dng (n, m). Further, these visual characteristics further include shapes, a color saturation, movement (e.g., blinking), an edge, brightness, a color difference, and an optical flow. In practice, the driver can see the outside ahead of the vehicle, as shown in FIG. 7B.

In contrast, the speaker 19 outputs the alarm from the direction where the object that should be observed by the driver is present. A person unconsciously sees a direction where there is a sound. The alarm can be outputted with the auditory characteristics being changed depending on the risk degree dng (n, m). Here, the auditory characteristics include a sound volume, a sound tone, a sound length, a sound quality, or a combination of the foregoing characteristics.

As explained above, the driving assistance system 11 computes and compares the actual driver's gaze distribution with the ideal gaze probability distribution. Therefore, when a driver does not see a sharp curve ahead of the traveling direction, it can be notified that the risk is present because of the sharp curve present ahead of the vehicle. Further, the first gaze probability-distribution computation unit 35 and the second gaze probability-distribution computation unit 37 compute the driver's ideal gaze probability distribution not only by using the present image information, but also by using the image information accumulated by the visual-field-image accumulation unit 33. If the driver sees the position of the sharp curve once, the notification of the risk is thereby not outputted for the following given period even though the driver sees the position no more. Therefore, this helps prevent the secondary risk that may occur because the driver continues observing the specific object.

(Others)

(i) In the above embodiment, the first gaze probability-distribution computation unit 35 computes the top-down gaze probability distribution based on the image information accumulated by the visual-field-image accumulation unit 33. However, if the bottom-up gaze probability distribution computed by the second gaze probability-distribution computation unit 37 is consistent with the image photographed by the front monitor camera 15, the image photographed by the front monitor camera 15 itself can be directly used for computing the top-down gaze probability distribution. This modified structure can compute the more accurate top-down gaze probability distribution, while obtaining the same effect as the above embodiment.

(ii) In the visual-field-image accumulation unit 33 of the above embodiment, the edge extraction unit 33b extracts edge portions from the visual-field images extracted by the visual-field center-image extraction unit 33a, while the luminance extraction unit 33c extracts the high luminance portions from the visual-field images extracted by the visual-field center-image extraction unit 33a. Further, another extraction unit can be provided for extracting characteristics based on a color saturation or an optical flow. Thus extracted information can be individually stored in a dedicated buffer, so it can be designed that the first gaze probability-distribution computation unit 35 or the second gaze probability-distribution computation unit 37 can use the individually stored information.

(iii) In the above embodiment, the first gaze probability-distribution computation unit 35 computes the top-down gaze probability distribution based on the image information accumulated by the visual-field-image accumulation unit 33. However, further, the driving assistance system 11 can interface with a navigation device, so the first gaze probability-distribution computation unit 35 can compute the top-down gaze probability distribution by obtaining information relating to the road shapes from the navigation device. This structure can obtain the more accurate information such as degrees in curves of the roads to thereby compute more accurate top-down gaze probability distribution.

(iv) In the above embodiment, the output control unit 45 causes the speaker 19 to output an alarm. However, it can be designed that the sound notifies the direction of the object that should be observed or the object itself. In detail, "confirm the signal ahead of the vehicle on the right," or "confirm the outside of the curve ahead of the vehicle," can be also outputted for notifying the driver of the object that should be observed.

It will be obvious to those skilled in the art that various changes may be made in the above-described embodiments of the present invention. However, the scope of the present invention should be determined by the following claims.

What is claimed is:

1. A driving assistance system provided in a vehicle that a driver operates, the system comprising:
   a detection unit that detects a distribution of a driver's gaze;
   an ideal computation unit that computes an ideal probability distribution of a driver's gaze, from the distributions detected in a past and information, wherein the information is derived from the vehicle and a periphery surrounding the vehicle, the ideal computation unit including
      an imaging unit that obtains image information ahead of the vehicle;
      a visual-field-image accumulation unit that accumulates image information corresponding to a driver's visual-field from the obtained image information and the detected distributions;
      a first computation unit that computes a probability distribution of a driver's gaze required for steering operation for traveling a road after obtaining a shape of the road from the accumulated image information, to thereby output a first result;
      a second computation unit that computes a probability distribution of a driver's gaze expected from a visual characteristic of the accumulated image information, to thereby output a second result; and
      an addition unit that adds up the outputted first result and the outputted second result to thereby obtain the ideal gaze probability distribution;
   a risk determination unit that determines presence of a risk when a difference between the detected distribution and the computed ideal probability distribution exceeds a given threshold; and
   an output unit that outputs a result determined by the risk determination unit.

2. The driving assistance system of claim 1, wherein the visual-image accumulation unit retains an elapsed period that elapses since the image information is updated with respect to each position on which a driver's gaze is, and
wherein the first computation unit computes the probability distribution by using the retained elapsed period so that the updated image information with respect to each position obtains a greater value as the updated image information becomes older.

3. The driving assistance system of claim 1, wherein the first computation unit computes the probability distribution of the driver's gaze required for the steering operation using the image information ahead of the vehicle obtained by the imaging unit, instead of the accumulated image information.

4. The driving assistance system of claim 1, wherein the first computation unit further obtains map information and computes the probability distribution of the driver's gaze required for the steering operation additionally using the obtained map information.

5. The driving assistance system of claim 1, wherein the visual characteristic used by the second computation unit includes at least one of a luminance, a color saturation, an edge strength, a color difference, and an optical flow.

6. The driving assistance system of claim 1, wherein the risk determination unit determines the presence of the risk with respect to each of a plurality of regions, and designates as a not-cared region a given region where a difference between the detected distribution and the computed probability distribution exceeds the given threshold, and
wherein the output unit outputs information for distinguishing the designated not-cared region.

7. The driving assistance system of claim 6, wherein the output unit includes a windshield display for indicating a marker, and the output unit causes the windshield display to indicate the marker so that the designated not-cared region is seen forward of the indicated marker from a viewpoint of the driver.

8. The driving assistance system of claim 7, wherein, when the output unit causes the windshield display to indicate the marker, the visual characteristic for the indicated marker is changed based on the difference between the detected distribution and the computed probability distribution.

9. The driving assistance system of claim 6, wherein the output unit includes a speaker and the output unit causes the speaker to output an alarm so that the alarm is outputted from a direction of the designated not-cared region.

10. The driving assistance system of claim 9, wherein, when the output unit causes the speaker to output the alarm, an auditory characteristic for the outputted alarm is changed based on the difference between the detected distribution and the computed probability distribution.

11. The driving assistance system of claim 6, wherein the output unit includes a speaker and the output unit causes the speaker to output an alarm that causes the driver to recognize the designated not-cared region.

* * * * *